(12) United States Patent
Nautiyal et al.

(10) Patent No.: US 9,057,091 B2
(45) Date of Patent: Jun. 16, 2015

(54) SYNERGISTIC COMPOSITION USEFUL AS MICROBIOLOGICAL GROWTH MEDIUM FOR RAPID SCREENING OF PHOSPHATE ACCUMULATING MICROORGANISMS

(75) Inventors: Chandra Sekhar Nautiyal, Lucknow (IN); Vasvi Chaudhry, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 579 days.

(21) Appl. No.: 13/187,046

(22) Filed: Jul. 20, 2011

(65) Prior Publication Data

US 2012/0028295 A1 Feb. 2, 2012

(30) Foreign Application Priority Data

Jul. 20, 2010 (IN) .......................... 1693/DEL/2010

(51) Int. Cl.
*C12Q 1/00* (2006.01)
*C12Q 1/04* (2006.01)
(52) U.S. Cl.
CPC . *C12Q 1/04* (2013.01); *C12Q 1/045* (2013.01)
(58) Field of Classification Search
CPC ............. A61K 38/51; C12N 9/88; C12Q 1/04; C12Q 1/045; C12Y 402/02011; H01M 4/8647; H01M 4/88; H01M 4/96; H01M 8/0234; H01M 8/0239; H01M 8/16; Y02E 60/527
See application file for complete search history.

(56) References Cited

PUBLICATIONS

Florentz et al., *Screening for Phosphate Accumulating Bacteria isolated from Activated Sludge*, 5 Environmental Technology Letters 457-463 (1984).

Lin-lin et al., *Phosphorus accumulation by bacteria isolated from a continuous-flow two-sludge system*, 19 Science Direct 391-395 (2007).

Onda et al., *Isolation and characterization of a Gram-positive polyphosphate-accumulating bacterium*, 48 J. Gen. Appl. Microbiol. 125-133 (2002).

Tobin et al., *Polyphosphate Accumulation by Pseudomonas putida CA-3 and Other Medium-Chain-Length Polyhydroxyalkanoate-Accumulating Bacteria under Aerobic Growth Conditions*, 73(4) Applied and Environmental Microbiology 1383-1387 (Feb. 2007).

*Primary Examiner* — Debbie K Ware
(74) *Attorney, Agent, or Firm* — Buchanan Ingersoll & Rooney PC (57) ABSTRACT

Screening isolates for phosphate accumulation by quantitative methods requires investment of time, labor and chemicals. There has been paucity of a medium and method for screening phosphate-accumulating microorganisms (PAOs) from the environment. Therefore, a new screening strategy is needed towards isolating effective PAOs in environments with diverse microbial populations and limited organic resources, where it is possible that PAOs are often out-competed by organisms capable of utilizing available nutrients more rapidly. In view of these problems, a medium optimal for an efficient screening of P-accumulating microorganisms was developed, which is rapid and allows many PAOs to be screened. Thus, the present invention utilizes Toluidine Blue-O (TBO) a blue colored dye, which decolorizes due drop in the concentration of phosphate in the medium, as an indicator to quickly evaluate the P-accumulating microorganisms based upon visual observations. Fast decolorization of the dye is an indicator of a superior phosphate accumulating microbe. Therefore, colorimetric reaction using PAM-TBO of the present work was further applied in a novel, extremely high-throughput manner to detect individual microbial isolates, growing on a PAM Petri plate. Adaptation of PAM-TBO assay in screening PAOs in environmental samples for microtitre plate assay enhanced the effectiveness of the assay system efficiently and effectively.

9 Claims, 4 Drawing Sheets

SYNERGISTIC COMPOSITION USEFUL AS MICROBIOLOGICAL GROWTH MEDIUM FOR RAPID SCREENING OF PHOSPHATE ACCUMULATING MICROORGANISMS

FIELD OF THE INVENTION

The present invention relates to a synergistic composition useful as microbiological growth medium for rapid screening of phosphate accumulating microorganisms. In particular, the present invention provides a medium and method for screening phosphate-accumulating microorganisms (PAOs) from environments with diverse microbial populations and limited organic resources. Further, the present invention provides a method for preferential screening of phosphate-accumulating microorganisms which is based upon visual observations and not on quantitative analysis thus eliminating investment of time, labour and chemicals.

BACKGROUND OF INVENTION AND DESCRIPTION OF PRIOR ART

Microorganisms play a key role in phosphate circulation in the biosphere [Schink B (2005) Biological cycling of phosphorus. Met Ions Biol Syst 43, 131-151]. Their ability to accumulate and utilize inorganic polyphosphates (polyP) and orthophosphate (Pi) as phosphate reserves is one of the mechanisms of adaptation to changing environmental conditions [Kulaev I S, Vagabov V M, Kulakovskaya T V (2004): The biochemistry of inorganic polyphosphates. Wiley, Chichester. $2^{nd}$ Edn.]. In recent years, due to rapid industrialization, urbanization, and population growth, water eutrophication i.e. excessive algal growth and related negative consequences in the surface water system has resulted in negative environmental effects. Obligatory anaerobic treatment of domestic and agro-industrial wastewater releases large amounts of phosphorus and nitrogen into wastewater. These nutrients are directly responsible for eutrophication of rivers, lakes, and seas worldwide [Lau P S, Tam N F Y, Wong Y S (1997) Wastewater nutrients (N and P) removal by carrageenan and alginate immobilized *Chlorella vulgaris*. Environ. Technol. 18, 945-951; Tre' panier C, Parent S, Comeau Y, Bouvrette J (2002). Phosphorus budget as a water quality management tool for closed aquatic mesocosms. Water Res. 36, 1007-1017]. Thus, removal of phosphorus from domestic and industrial wastewaters is central in curbing the water pollution problem of eutrophication.

Biological phosphate removal processes have been attracting attention in recent years because of low investment and operational costs compared with chemical precipitation processes [Pijuan M, Guisasola A, Baeza J A, Carrera J, Casas C, Lafuente J (2005) Aerobic phosphate release linked to acetate uptake: Influence of PAO intracellular storage compounds. Biochemical Engineering Journal. 26 (2-3)184-190 Engineering Bioreaction Systems: A Spanish Perspective; Michael H. Gerardi (2006) Wastewater Bacteria ISBN: 978-0-471-20691-0]. Bacteria involved in "enhanced biological phosphate removal" (EBPR) from waste accumulate large amounts of polyP, while some archaea and bacteria accumulate Pi [Smirnov A, Suzina N, Chudinova N, Kulakovskaya T, Kulaev I (2005) Formation of insoluble magnesium phosphates during growth of the archaea *Halorubrum distributum* and *Halobacterium salinarium* and the bacterium *Brevibacterium antiquum*. FEMS Microbiol. Ecol. 52, 129-137; Ryazanova L P, Smirnov A V, Kulakovskaya T V, Kulaev I S, (2007) Decrease of phosphate concentration in the medium by *Brevibacterium casei* cells. Microbiology. 76, 752-758; Ryazanova L P, Suzina N E, Kulakovskaya T V, Kulaev I S (2009) Phosphate accumulation of *Acetobacter xylinum*. Arch. Microbiol. 191, 467-471]. For understanding the role of bacteria in the phosphate turnover in nature and technology, it is important to reveal new species capable of effective phosphate accumulation. Independent studies have shown what is presumably the identical wild type isolated from activated sludge to have vastly different Phosphate uptake capabilities under laboratory conditions.

One striking feature which differs in these bioassays is the use of different media to conduct the experiments. Although mixed liquor is derived from the natural environment of phosphate-accumulating microorganisms (PAOs), synthetic media of different formulations are popular for experimental study of PAOs, due to their controllable consistencies.

Phosphate accumulating microorganisms are routinely screened using the following media—

M9 Medium [Minimal Medium 9]:
   Composition: ($L^{-1}$) Glucose, 4 g; NaCl, 0.5 g; $NH_4Cl$, 1 g; $CaCl_2$, 0.014 g; $MgSO_4$, 0.25 g; $Na_2HPO_4$, 12.8 g; $KH_2PO_4$, 3 g.
Reference: Sambrook, J., E. F. Fritsch, and T. Maniatis. 1989. Molecular cloning: a laboratory manual, 2nd ed. Cold Spring Harbor Laboratory Press, Cold Spring Harbor, N.Y.
NM Medium [Nakamura et al., 1995]:
   Composition: ($L^{-1}$) Glucose, 0.5 g; Peptone, 0.5 g; Monosodium glutamate 0.5 g, Yeast extract, 0.5 g; $KH_2PO_4$, 0.44 g; $(NH_4)_2SO_4$, 0.1 g; $MgSO_4.7H_2O$, 0.1 g. pH of the medium is adjusted to 7.0 with dilute NaOH solution. Reference: Nakamura K, Hiraishi A, Yoshimi Y, Kawaharasaki M, Masuda K, Kamagata Y (1995) *Microlunatus phosphovorus* gen. nov., sp. nov., a New Gram-Positive Polyphosphate-Accumulating Bacterium Isolated from Activated Sludge. International Journal of Systematic Bacteriology, 45 (1) 17-22.
SWW Medium [Synthetic Waste Water Medium]:
   Composition: ($L^{-1}$ tap water) Acetate, 177 mg; Peptone, 55 mg; $CaCl_2$, 14.4 mg; $MgSO_4.7H_2O$, 95.0 mg; $(NH_4)_2SO_4$, 12.7 mg; and $KH_2PO_4$, 21.1 mg.
Reference: Zhang H, Sekiguchi Y, Hanada S, Hugenholtz P, Kim H, Kamagata Y, Nakamura K (2003) *Gemmatimonas aurantiaca* gen. nov., sp. nov., a Gram-negative, aerobic, polyphosphate-accumulating micro-organism, the first cultured representative of the new bacterial phylum Gemmatimonadetes phyl. nov. International Journal of Systematic and Evolutionary Microbiology, 53, 1155-1163.

Literature reports depict that various mixed liquor and synthetic media have been used in microbial Phosphate uptake research [Ohtake H, Takahashi K, Tsuzuki Y, Toda K (1985) Uptake and release of phosphate by a pure culture of *Acinetobacter calcoaceticus*. Water Res. 19 (12) 1587-1594; Appeldoorn K J, Kortsee G J J, Alexander J B Z (1992) Biological phosphate removal by activated sludge under defined conditions. Water Res. 26 (4) 453-460; Muyima N Y O, Cloete T E (1995) Phosphate uptake by immobilized *Acinetobacter calcoaceticus* in a full scale activated sludge plant. J. Ind. Microbiol. 15, 19-24; Morohoshi, T., Yamashita T, Kato J, Ikeda T, Takiguchi N, Ohtake H, Kuroda A (2003) A method for screening phosphate-accumulating mutants which remove phosphate efficiently from synthetic wastewater. J. Biosci. Bioeng., 95(6), 637-640]. However, no conclusive studies have been conducted to compare the effect of these media types on bacterial response, or if a particular medium causes results to be inflated or exaggerated. The use of synthetic media and mixed liquor in different studies resulted in conflicting reports on the Phosphate uptake capabilities of PAOs isolated from the environment.

Thus, from the findings of the prior art it may be summarized that there is a paucity of a medium and method for screening phosphate-accumulating microorganisms (PAOs) from the environment. Therefore, a new screening strategy is needed towards isolating effective PAOs in environments with diverse microbial populations and limited organic resources. It is noteworthy to mention here that PAOs are often out-competed by organisms capable of utilising available nutrients more rapidly. Further, screening microbial isolates for phosphate accumulation by quantitative methods requires investment of time, labour and chemicals. In view of these problems, the inventors of the present invention realized that there exists a dire need to develop a medium optimal for efficient screening of P-accumulating microorganisms, which is rapid and allows many PAOs to be screened, based upon visual observations.

OBJECTS OF THE INVENTION

The main object of the present invention is thus to provide a synergistic composition that serves as a medium for rapid screening of phosphate-accumulating microorganisms.

Another object of the invention is to provide a process for screening phosphate accumulating microorganisms, which is based upon visual observations and not on quantitative analysis thus eliminating investment of time, labour and chemicals.

Still another object of the present invention is to provide a composition which is useful for screening the effects of physical parameters like carbon, nitrogen and salts on phosphate accumulation in soil environments where physiological factors may constitute a limitation for phosphate accumulation.

SUMMARY OF THE PRESENT INVENTION

The present invention relates to a synergistic microbiological growth medium composition which is useful for rapid screening of phosphate-accumulating microorganisms. The invention further provides a process for screening phosphate accumulating microorganisms, which is based upon visual observations and not on quantitative analysis thus eliminating investment of time, labour and chemicals Thus, the present method is rapid and allows many PAOs to be screened. Toluidine Blue-O (TBO) is a blue coloured dye which decolorises due to the drop in the concentration of phosphate in the medium, thus acting as an indicator to quickly evaluate the P-accumulating microorganisms. Therefore, a defined medium PAM-TBO for screening Phosphate-accumulating microorganisms, based upon visual observations was developed. Fast decolorization of the dye is an indicator of a superior phosphate accumulating microbe. Therefore colorimetric reaction using PAM-TBO of the present work was further applied in a novel, extremely high-throughput manner to detect the individual microbial isolates, growing on a PAM petri plate. Adaptation of PAM-TBO assay in screening PAOs in environmental samples for microtitre plate assay enhanced the effectiveness of the assay system efficiently and effectively.

Further, the composition of the present invention is useful in screening phosphate accumulating strains better suited for soil environments where physiological factors may constitute a limitation for phosphate accumulation, for the screening phosphate accumulation defective mutants. It also serves for the initial screening of phosphate accumulators isolated from environments such as soil, water and activated sludge represented by fungi, actinomycetes and bacteria.

Accordingly, the present invention provides a synergistic composition useful as microbiological growth medium for rapid screening of phosphate accumulating microorganisms, wherein the said composition comprising:

| component | g/l |
|---|---|
| Sodium citrate | 1.0 to 10.0 |
| $(NH_4)_2SO_4$ | 1.0 to 5.0 |
| NaCl | 0.1 to 10.0 |
| $CaCl_2$ | 0.1 to 1.0 |
| $MgSO_4 \cdot 7H_2O$ | 0.1 to 1.0 |
| $Na_2HPO_4$ | 5.0 to 15.0 |
| $KH_2PO_4$ | 1.0 to 30.0 |
| Maltose | 0.05 to 10.0 |
| Toluidine Blue-O | 0.01 to 0.1. |

The invention further provides a process for screening phosphate accumulating microorganisms using the said composition, wherein the said process comprising the steps of:
[a] incubating the microorganism in the growth medium composition of claim 1 for a period of 1 to 15 days at a temperature of 15 to 46 degree C. under shaking to obtain a culture;
[b] harvesting the culture of step [a] to obtain a supernatant;
[c] measuring the optical density of the supernatant obtained in step [b] at 625 nm to assess decolorization of the dye as an indicator of a superior phosphate accumulating microbe.

These and other aspects of the present invention will become apparent to those skilled in the art after a reading of the following description of the preferred embodiment when considered with the drawings, as they support the claimed invention.

BRIEF DESCRIPTION OF THE ACCOMPANYING DRAWINGS

Phosphate accumulation ability of the strain NBRI1213 was studied using PAM, Minimal medium (M9), NM medium and synthetic waster water broth up to 10 days (FIG. 1). The result suggests that formulated PAM medium was about 2.5 to 7.0 fold more efficient as compared to NM medium, M9 medium and SWW medium respectively. The ability of the strain to accumulate phosphate in PAM was also maintained at a higher level throughout the duration of 10 days. This further augments well for the use of PAM as an efficient phosphate accumulation medium over other media and also that PAM should serve as a synergistic composition for qualitative screening of phosphate-accumulating microorganisms.

FIG. 3A illustrates that as compared with control PAM-TBO, NBRI1213 MTCC 8708 demonstrated diverse level of phosphate accumulation activity in the presence of various carbon glucose (3B), sorbitol (3C), glycerol (3D) and sucrose (3E). Similarly, diversity in phosphate accumulation using varied nitrogen sources are depicted as $C_2H_7NO_2$ (3F), $KNO_3$ (3G), $NH_4NO_3$ (3H), $NH_4Cl$ (3I) and for salts it is shown as $Na_2CO_3$ (3J), KCl (3K), $Na_2SO_4$ (3L) and $MnSO_4$ (3M). The pattern of phosphate accumulation by NBRI1213 MTCC 8708 in qualitative assay with PAM-TBO correlated well with the quantitative assay. The potential of Tn5 mutants of NBRI1213 viz; NBRI1213-4052 (3N) and NBRI1213-4053 (3O) for phosphate accumulation was assessed by incubating them in PAM-TBO at 28° C. for 2 days

DETAILED DESCRIPTION OF THE PRESENT INVENTION

The instant invention provides a synergistic medium composition useful as microbiological growth medium which is optimal for efficient screening of phosphate-accumulating microorganisms. The screening process of the invention is rapid and allows many PAOs to be screened, based upon visual observations. In another aspect, the present invention aids in isolating effective PAOs in environments with diverse microbial populations and limited organic resources, where it is possible that PAOs are often out-competed by organisms capable of utilising available nutrients more rapidly.

It may be noted that screening microbial isolates for phosphate accumulation by quantitative methods requires investment of time, labour and chemicals. Toluidine Blue-O (TBO) is a blue coloured dye which decolorizes due to the drop in the concentration of phosphate in the medium, thus acting as an indicator to quickly evaluate the P-accumulating microorganisms. Therefore, a defined medium PAM-TBO for rapid screening of phosphate-accumulating microorganisms, based upon visual observations was developed. Fast decolorization of the dye is an indicator of a superior phosphate accumulating microbe. Therefore, colorimetric reaction using PAM-TBO of the present work was further applied in a novel, extremely high-throughput manner to detect individual microbial isolates, growing on a PAM petri plate. Adaptation of PAM-TBO assay in screening PAOs in environmental samples for microtitre plate assay enhanced the effectiveness of the assay system efficiently and effectively.

Medium Composition and Preparation

Preliminary work to optimize the medium was started with Minimal medium 9 (M9) salts. Subsequent replacement of the glucose was done with sucrose, sorbitol, mannitol, maltose, arabinose, lactose, sodium benzoate, sodium acetate and sodium citrate. Ammonium chloride as nitrogen source was replaced with magnesium nitrate, ammonium acetate, ammonium nitrate, sodium nitrate, potassium nitrate, aluminum ammonium sulphate and ammonium sulphate and combination of salts of magnesium and calcium were optimized to prepare complete defined medium for growth and screening of PAOs. Water for all media was deionized and double distilled prior to use. For quantitative analysis, composition of the complete defined medium (PAM) was (g/L) Sodium citrate, 4; NaCl, 0.5; $(NH_4)_2SO_4$, 2.5; $CaCl_2$, 0.25; $MgSO_4$, 0.25; $Na_2HPO_4$, 12.8; $KH_2PO_4$, 3; Maltose, 0.01; and Agar, 20 (for initial screening of PAOs on Petri-plates). For qualitative screening of PAOs Toluidine Blue-O dye (0.025 g/L) was added and the medium was designated as PAM-TBO. Stock solutions of Maltose, $CaCl_2$ and $MgSO_4$ were autoclaved for 20 min at 10 psi or filter sterilized individually with a 0.2-mm-poresize filter and aseptically added and mixed thoroughly prior to inoculation of culture. For comparative studies PAM was tested against M9, NM (Nakamura et al., 1995) and synthetic waste water (SWW) (Ohtake et al., 1996). Compositions of M9 was (g/L) $Na_2HPO_4$, 12.8; $KH_2PO_4$, 3.0; NaCl, 0.5; $NH_4Cl$, 1.0; Glucose, 2.0; $MgSO_4.7H_2O$, 0.4940; $CaCl_2.2H_2O$, 0.0152; NM was (g/L) Glucose, 0.5; peptone, 0.5; monosodium glutamate, 0.5; yeast extract, 0.5; $KH_2PO_4$, 0.44; $(NH_4)_2SO_4$, 0.1; $MgSO_4.7H_2O$ and SWW (g/L) was Peptone, 0.2; citric acid, 0.2; yeast extract, 0.02; $NaHCO_3$, 0.075; $MgSO_4.7H_2O$, 0.15; $CaCl_2.2H_2O$, 0.05; NaCl, 0.1; $KH_2PO_4$, 0.053.

Optimization of Color Based Method for Qualitative Screening of PAOs

Qualitative (Toluidine Blue-O color based qualitative estimation of phosphate accumulation) and quantitative analyses (quantitative estimation of phosphate accumulation as Pi) in broth were carried out by using 50 ml of PAM in a 150 mL test tube inoculated in triplicate with the bacterial strain (500 μL inoculum with approximately 1 to $2\times10^9$ cfu/mL). Autoclaved, uninoculated medium served as controls. For qualitative estimation of TBO in PAM-TBO, the optical density of the culture supernatant was measured at 625 nm. For the quantitative analysis, phosphate accumulated in the culture biomass was extracted by using the method of Rao et al. (1985) and estimated by the Mo-Blue method (Muyima and Cloete, 1995) at 820 nm, by using Milton Roy Spectronic 20D1, USA.

Development of High Throughput Microtiter Plate Based Method

Bacterial cultures were individually cultivated in the microtiter plates with 4 replicates. Upper 4 wells contained 200 μl PAM-TBO, while lower 4 wells contained 200 μl PAM medium. Initially 20 μl inoculum prepared in NB was inoculated in the selected wells of the microtiter plate and also served as blank for the plate reader. Typically, wells in column 12 on each plate remained unseeded, as these 8 wells acted as negative background controls during subsequent analyses. When all the selected wells were seeded, the microtiter plates were covered with its original lid, sealed with parafilm, placed inside an incubator and incubates statically for 24 h at 28° C. To remove the interference with O.D. of bacterial cells, after incubation the microtiter plates were centrifuged for 15 min at ~1800×g (Sigma 3-16 K). After centrifugation, the media removed from the wells was then transferred to fresh microtiter plates. The resulting color production was quantitated in terms of the absorbance (the optical density at 625 nm [$OD_{625}$]) in a microtiter plate reader (Biotex). To reduce the effects of plate-to-plate variations and day-to-day variations, *Escherichia coli* NBRI-28 (MTCC 1302 equivalent) with low phosphate accumulation and NBRI1213 MTCC 8708 with high phosphate accumulation ability properties as controls were incorporated on each assay plate and two designated control plates were included in each screening session. Plate-based controls were incorporated; and assay wide controls were included to determine background levels, signal-to-noise ratios, and standards for normalization. Using the protocol described as above no statistically significant differences were noted when comparing all pairs of rows to each other (P>0.05), under the designed experimental conditions.

Flow of Steps to Arrive at the Present Invention:

1. A synergistic medium composition useful as microbiological growth medium which is optimal for efficient screening of phosphate-accumulating microorganisms was developed by optimizing the carbon, nitrogen and salts sources.
2. This synergistic medium composition was optimized as microbiological growth medium for preferential screening of phosphate-accumulating microorganisms in both liquid broth and solid agar based medium.
3. Screening of microbial isolates for phosphate accumulation by quantitative methods requires investment of time, labour and chemicals. Hence, Toluidine Blue-O (TBO) a blue coloured dye based medium, PAM-TBO was developed for rapid screening of phosphate-accumulating microorganisms, based upon visual observations. Fast decolorization of the dye is an indicator of a superior phosphate accumulating microbe.
4. Colorimetric reaction using PAM-TBO to detect phosphate accumulating organisms was further applied in a novel, extremely high-throughput manner in microtitre plates which enhanced the effectiveness of the assay system efficiently and effectively.

The synergistic composition of the present invention is not a mere admixture of the ingredients used resulting in aggregation of their properties but a synergistic mixture having enhanced properties resulting in efficient and rapid identification of phosphate accumulating microorganisms.

In an embodiment, the present invention provides a synergistic microbiological growth medium composition designated, "PAM" which comprises:

| Component | grams/liter |
| --- | --- |
| Sodium citrate | 4.0 |
| $(NH_4)_2SO_4$ | 2.5 |
| NaCl | 0.5 |
| $CaCl_2$ | 0.25 |
| $MgSO_4 \cdot 7H_2O$ | 0.25 |
| $Na_2HPO_4$ | 12.8 |
| $KH_2PO_4$ | 3.0 |
| Maltose | 1.0 |

In another embodiment of the present invention, the ingredients used may be of commercial grade. However, the use of purer ingredients such as that of laboratory grade will result in better and reproducible results.

In still another embodiment, the invention provides a rapid and efficient method for screening of phosphate accumulating microorganisms.

In yet another embodiment, the invention provides a qualitative method for easy and fast screening of phosphate accumulating comprising a synergistic growth medium composition containing essential TBO dye in the range of 0.01 to 0.1 g/L.

In still another embodiment of the present invention is provided a kit for the screening of phosphate accumulating microorganisms containing TBO in a growth medium, comprising:

| Component | grams/liter |
| --- | --- |
| Sodium citrate | 4.0 |
| $(NH_4)_2SO_4$ | 2.5 |
| NaCl | 0.5 |
| $CaCl_2$ | 0.25 |
| $MgSO_4 \cdot 7H_2O$ | 0.25 |
| $Na_2HPO_4$ | 12.8 |
| $KH_2PO_4$ | 3.0 |
| Maltose | 1.0 |
| Toluidine Blue-O | 0.025 |

In yet another embodiment of the present invention, the growth medium composition comprises:

| component | grams/liter |
| --- | --- |
| Sodium citrate | 1 to 10 |
| $(NH_4)_2SO_4$ | 1 to 5 |
| NaCl | 0.1 to 10 |
| $CaCl_2$ | 0.1 to 1.0 |
| $MgSO_4 \cdot 7H_2O$ | 0.1 to 1.0 |
| $Na_2HPO_4$ | 5 to 15 |
| $KH_2PO_4$ | 1 to 30 |
| Maltose | 0.05 to 10 |
| Toluidine Blue-O | 0.01 to 0.1 |

In still another embodiment of the present invention, screening of phosphate-accumulating microorganisms is done by incubation at 15-45° C. preferably 28° C., for 1-15 days, preferably 2 days.

In yet another embodiment of the present invention, screening of phosphate-accumulating microorganisms shows at least 100 mM Pi Content per gm biomass of microorganism, in a concentration of microorganism ranging between about Log 3 to 10 colony forming unit (CFU)/ml, where for example, Log 3=1,000.

In still another embodiment of the present invention, the microorganisms are preferably bacteria.

In a further embodiment of the present invention, the growth medium composition serves as a synergistic composition for preferential screening of phosphate-accumulating microorganisms that grow on the culture medium, under the conditions chosen, in the presence of the other microorganism on that particular plate.

In another embodiment of the present invention, the screening is useful to quickly screen phosphate-accumulating microorganisms being based upon visual observations, and not on quantitative analysis thus eliminating investment of time, labour and chemicals.

In still another embodiment of the present invention, the synergistic composition is useful for screening the effects of physical parameters like carbon, nitrogen and salts on phosphate accumulation based upon visual observation in search of phosphate accumulating strains better suited for soil environments where physiological factors may constitute a limitation for phosphate accumulation.

In yet another embodiment of the present invention, the growth medium composition is useful for screening of phosphate accumulating defective mutants.

In still another embodiment of the present invention, the phosphate accumulators are isolated from environments such as soil, water and activated sludge and represented by fungi, actinomycetes and bacteria.

In yet another embodiment of the present invention, the growth medium composition serves for screening environmental samples by a process which is automated and controlled by a microprocessor or other computer control devices.

EXAMPLES

The invention is described with reference to the examples which are provided by way of illustration only and therefore should not be construed to limit the scope of the present invention.

Example 1

Isolation of PAOs has been reported to be problematic due to their slow growth rates. This discrepancy has limited our understanding of the PAOs. In environments with diverse microbial populations and limited organic resources, it is possible that PAOs are often out-competed by organisms capable of utilising available nutrients more rapidly. The only avenues currently available for the study of uncultured bacteria are cultivation-independent molecular ecological techniques that have proved to be very powerful for the study of bacteria in their natural settings. Parallel study of laboratory cultures would, however, strongly complement molecular ecological investigations and enhance research into the roles of soil bacteria and their biotechnological potentials. Another limiting factor in the isolation of PAO species from activated sludge is the lack of suitable media that would support the growth of all viable nutritional types. The availability of pure cultures will however greatly simplify such studies by our ability to grow these microorganisms in pure culture with simple media. It has been reported that isolated PAOs do not show the same characteristics in their Phosphate uptake capabilities under laboratory conditions, compared with full-scale in situ studies. Due to the lack of information available about the influence of different media types on Phosphate removal experimentation this experimental study was conducted to determine the effect of different media types on isolation of PAOs and Phosphate removal.

In our attempt to formulate a defined media for screening Phosphate-accumulating microorganisms quantitative estimation of phosphate accumulation was carried out, using Phosphate-accumulating bacterium NBRI1213 MTCC 8708 as a reference, grown on shaker (180 rpm) at 28° C. for 48 h in 50 ml medium. After incubation, the cells were harvested by centrifugation at 10,000×g for 10 min at 4° C. and used for extraction of phosphorus. Total poly Pi was extracted by the method described by Rao N N, Roberts M F, Torrianil A (1985) Amount and Chain Length of Polyphosphates in *Escherichia coli*. Depend on Cell Growth Conditions J. Bacteriol. 162 (1), 242-247 p, based on the insolubility of poly Pi in alkaline hypochlorite. NaF (1 mM) was added, and the pH of the reagent was adjusted to 9.8. The cells (about $10^9$ cells per ml) were collected by centrifuging 50 ml of culture at 10,000×g for 10 min at 4° C. The cells were resuspended in 0.145 M NaCl containing 1 mM NaF, and the centrifugation was repeated. The washed pellet was suspended in 1 ml of alkaline hypochlorite reagent and incubated at 25° C. for 60 min. The insoluble fraction was collected by centrifugation at 27,000×g for 15 min. The fraction was suspended in 1 ml of a wash solution containing 1.5 M NaCl, 5 mM EDTA, and 1 mM NaF and adjusted to pH 4.6 with HCl. This suspension was centrifuged (27,000×g for 15 min), and the supernatant was discarded. The residue was solubilized in 1 ml of 0.154 M NaCl solution, adjusted to pH 7.0 and centrifuged at 10,000×g for 10 min, and the supernatant fluid was collected. This poly Pi extract was stored at 0 to 4° C.

The content of Pi was estimated by Mo-Blue method recited by Ohtomo R, Sekiguchi Y, Mimura T, Saito M and Ezawa T (2004) Quantification of polyphosphate: different sensitivities to short-chain polyphosphate using enzymatic and colorimetric methods as revealed by ion chromatography. Anal. Biochem. 328 (2), 139-146. 100 μL poly Phosphate solution was mixed with an equal volume of 2 N HCl and heated at 95° C. for 30 min. Then the solution was diluted to 300 μL with distilled water, mixed with 700 μL of the Mo-blue assay solution (6 parts of 0.42% $(NH_4)_6Mo_7O_{24}.4H_2O$ in 1 $NH_2SO_4$ and 1 part of 10% ascorbate), and the solution was made 5 mL with distilled water and incubated at 45° C. for 20 min. Pi concentration was determined based on absorbance at 820 nm with reference to the standard curve of 0-10 mM phosphate. Wet biomass value was used for calculations.

By varying the carbon sources, it was found that the type and amount of carbon source played an important role in phosphate accumulation (Table 1).

TABLE 1

Effect of different carbon sources on phosphate accumulation using NBRI1213 MTCC 8708

| C-Sources [4%] | Pi content (mM gm biomass$^{-1}$) |
|---|---|
| M9: controlmedium containing glucose | 27.06 ± 0.37 |
| Sucrose | 20.10 ± 0.93 |
| Sorbitol | 18.98 ± 0.76 |
| Mannitol | 16.92 ± 3.0 |
| Maltose | 13.25 ± 0.18 |
| L-Arabinose | 10.71 ± 0.72 |
| Lactose | 0.66 ± 0.0 |
| Sodium benzoate | 13.10 ± 0.77 |
| Sodium acetate | 21.3 ± 1.01 |
| Sodium citrate | 90.23 ± 8.76 |

Control M9 medium [M9] contained $I^{-1}$: Glucose, 4 g; NaCl, 0.5 g; $NH_4Cl$, 1 g; $CaCl_2$, 0.014 g; $MgSO_4$, 0.25 g; $Na_2HPO_4$, 12.8 g; $KH_2PO_4$, 3 g. The changed carbon sources are indicated in table 1 along with the Pi content (mM gm biomass$^{-1}$) which the bacteria accumulate in their presence. The data are the means of three independent experiments. It is apparent from the above table that amongst a range of carbon sources, in presence of sodium citrate NBRI1213 MTCC 8708 accumulated maximum phosphate with 90.23 mM per gm biomass. Thus, sodium citrate was used as the carbon source in further experiments.

The ability of nitrogen source in influencing the phosphate accumulation ability was checked by replacing $NH_4Cl$ with a range of nitrogen sources (Table 2).

TABLE 2

Effect of different nitrogen sources on phosphate accumulation using NBRI1213 MTCC 8708

| N sources | Pi content (mM gm biomass$^{-1}$) |
|---|---|
| M9C: control medium containing Sodium citrate | 90.23 ± 8.76 |
| M9C + $NH_4Cl$ (0.1%) | 90.23 ± 8.76 |
| M9C + $MgNO_3$ (0.1%) | 2.34 ± 0.43 |
| M9C + $C_2H_7NO_2$ (0.1%) | 24.15 ± 3.55 |
| M9C + $NH_4NO_3$ (0.1%) | 15.55 ± 1.20 |
| M9C + $NaNO_3$ (0.1%) | 0.955 ± 0.51 |
| M9C + $KNO_3$ (0.1%) | 4.4 ± 0.14 |
| M9C + $AlNH_4(SO_4)_2•12H_2O$ (0.1%) | 5.18 ± 0.47 |
| M9C + $(NH_4)_2SO_4$ (0.025%) | 2.75 ± 0.22 |

TABLE 2-continued

Effect of different nitrogen sources on phosphate
accumulation using NBRI1213 MTCC 8708

| N sources | Pi content (mM gm biomass$^{-1}$) |
|---|---|
| M9C + $(NH_4)_2SO_4$ (0.05%) | 6.74 ± 0.23 |
| M9C + $(NH_4)_2SO_4$ (0.1%) | 99.3 ± 1.80 |
| M9C + $(NH_4)_2SO_4$ (0.25%) | 103.65 ± 5.05 |
| M9C + $(NH_4)_2SO_4$ (0.5%) | 97.4 ± 1.86 |
| M9C + $(NH_4)_2SO_4$ (1%) | 48.56 ± 0.84 |

Control M9C medium [M9C] contains $I^{-1}$: Sodium citrate, 4 g; NaCl, 0.5 g; $NH_4Cl$, 1 g; $CaCl_2$, 0.014 g; $MgSO_4$, 0.25 g; $Na_2HPO_4$, 12.8 g $KH_2PO_4$, 3 g. The changed nitrogen sources are indicated in table 2 along with the Pi content (mM gm biomass$^{-1}$) which the bacteria accumulate in their presence. The data are the means of three experiments. It is observed that amongst the range of nitrogen sources, NBRI1213 MTCC 8708 accumulates phosphate efficiently in presence of $(NH_4)_2SO_4$. Phosphate accumulation ability further improved by increasing the concentration of $(NH_4)_2SO_4$ by 0.25% instead of 0.1% $(NH_4)_2SO_4$. Henceforth, in all the experiments $(NH_4)_2SO_4$ was used as the nitrogen source.

TABLE 3

Effect of different salts and their combinations on
phosphate accumulation using NBRI1213 MTCC 8708

| Salts (%) | Pi Content (mM gm biomass$^{-1}$) |
|---|---|
| M9CN: control medium | 103.65 ± 5.05 |
| M9CN + $MgCl_2$ (0.025) | 124.12 ± 2.66 |
| M9CN + $MgSO_4$ (0.025) | 116.0 ± 2.8 |
| M9CN + $MgNO_3$ (0.025) | 92.09 ± 5.28 |
| M9CN + $MgCO_3$ (0.025) | 60.23 ± 2.03 |
| M9CN + $CaCl_2$ (0.025) | 84.63 ± 0.62 |
| M9CN + $CaSO_4$ (0.025) | 54.72 ± 0.27 |
| M9CN + Ca$(NO_3)_2$ (0.025) | 58.08 ± 7.92 |
| M9CN + $CaCO_3$ (0.025) | 19.24 ± 0.68 |
| M9CN + $MgSO_4$ (0.025) + $CaCl_2$ (0.025) | 124.35 ± 13.05 |
| M9CN + $MgSO_4$ (0.025) + $CaCl_2$ (0.05) | 80.73 ± .685 |
| M9CN + $MgSO_4$ (0.025) + $CaCl_2$ (0.1) | 107.90 ± 14.29 |
| M9CN + $MgSO_4$ (0.025) + $CaCl_2$ (0.2) | 74.40 ± 5.90 |
| M9CN + $MgNO_3$ (0.025) + $CaCl_2$ (0.025) | 130.46 ± 6.31 |
| M9CN + $MgNO_3$ (0.025) + $CaCl_2$ (0.05) | 125.31 ± 3.05 |
| M9CN + $MgNO_3$ (0.025) + $CaCl_2$ (0.1) | 99.82 ± 1.55 |
| M9CN + $MgNO_3$ (0.025) + $CaCl_2$ (0.2) | 74.04 ± 3.48 |
| M9CN + $MgCl_2$ (0.025) + $CaCl_2$ (0.025) | 132.77 ± 2.96 |
| M9CN + $MgCl_2$ (0.025) + $CaCl_2$ (0.05) | 98.14 ± 19.01 |
| M9CN + $MgCl_2$ (0.025) + $CaCl_2$ (0.1) | 127.29 ± 2.60 |
| M9CN + $MgCl_2$ (0.025) + $CaCl_2$ (0.2) | 77.30 ± 5.40 |

Control M9CN medium [M9CN] contains $I^{-1}$: Sodium citrate, 4 g; NaCl, 0.5 g; $(NH_4)_2SO_4$, 2.5 g; $CaCl_2$, 0.014 g; $MgSO_4$, 0.25 g; $Na_2HPO_4$, 12.8 g $KH_2PO_4$, 3 g. Changes in salts in M9CN medium are indicated in table 3 along with their concentrations in the brackets. The data are the means of three experiments. After testing a range of salts to improve the phosphate accumulation ability of NBRI1213 MTCC 8708 it was observed that $MgCl_2$ at 0.025% in the presence of $CaCl_2$ at 0.025% had a better synergistic effect on phosphate accumulation activity, compared to other salts of magnesium and calcium (Table 3). The synergistic medium composition obtained from the hitherto executed experiments for quantitative estimation of phosphate accumulation was designated as NBRI medium.

To enhance the efficiency of the NBRI medium it was further supplemented with additional sugars as carbon sources as shown in Table 4.

TABLE 4

Effect of different sugars on phosphate
accumulation of NBRI1213 MTCC 8708

| Sugar sources (%) | Pi content (mM gm biomass$^{-1}$) |
|---|---|
| Control NBRI medium | 132.77 ± 2.96 |
| NBRI medium + Glucose (0.1) | 49.37 ± 3.09 |
| NBRI medium + Sucrose (0.1) | 63.97 ± 3.68 |
| NBRI medium + L-Arabinose (0.1) | 54.87 ± 1.44 |
| NBRI medium + Glycerol (0.1) | 32.94 ± 1.92 |
| NBRI medium + Mannitol (0.1) | 44.33 ± 1.36 |
| NBRI medium + Sorbitol (0.1) | 29.22 ± 3.79 |
| NBRI medium + Maltose (0.1) (PAM) | 141.49 ± 1.95 |

Control NBRI medium contains $I^{-1}$: Sodium citrate, 4 g; NaCl, 0.5 g; $(NH_4)_2SO_4$, 2.5 g; $CaCl_2$, 0.25 g; $MgSO_4$, 0.25 g; $Na_2$HPO4, 12.8 g $KH_2PO_4$, 3 g. Further supplementation of NBRI medium with additional sugars as carbon sources are indicated in table 4 along with their concentrations in the brackets. The data are the means of three experiments. The results demonstrate that further enrichment of the NBRI with 0.1% maltose enhanced the growth and phosphate accumulation ability of NBRI1213 MTCC 8708. The NBRI medium supplemented with 0.1% maltose as described in Table 4, formulated for an efficient quantitative estimation of phosphate accumulation was designated as Phosphate Accumulating Medium [PAM].

Figure 1:
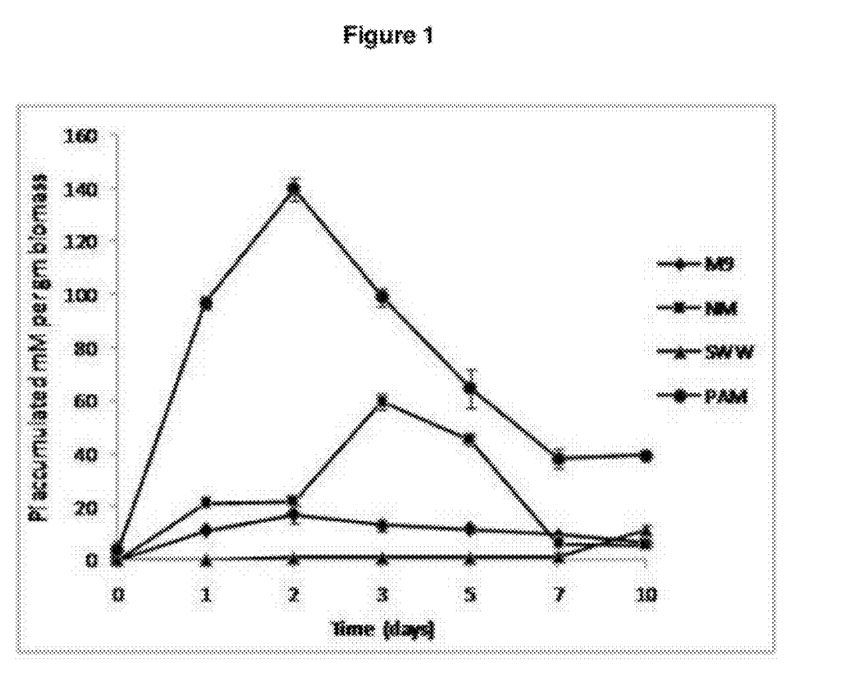
FIG. 1: Evaluation of the efficiency of different media for phosphate accumulation. Comparison was made to check the efficiency of known media used for phosphate accumulation based studies in known bacteria. The formulated media was found to improve the phosphate accumulation ability of the bacterium *Serratia marcescens* NBRI1213 (MTCC 8708).

Phosphate accumulation ability of the strain NBRI1213 was studied using PAM, Minimal medium (M9), NM medium and synthetic waster water broth up to 10 days (FIG. 1).

The result suggests that formulated PAM medium was about 2.5 to 7.0 fold more efficient as compared to NM medium, M9 media and SWW medium respectively. The ability of the strain to accumulate phosphate in PAM was also maintained at a higher level throughout the duration of 10 days. This further augments well for the use of PAM as an efficient phosphate accumulation medium over other media and also that PAM should serve as a synergistic composition for qualitative screening of phosphate-accumulating microorganisms.

Example 2

Perhaps only 1 to 10% of the existing soil bacterial species are known. It is possible that a group of microorganisms with a particular function consists of populations of many different species, but virtually nothing is known about the dynamics of these populations and their regulation in soil. Therefore in an attempt while developing the PAM media for qualitative screening of phosphate-accumulating microorganisms, screening of several media for their efficiency to select phosphate-accumulating microorganisms preferentially on petri-plates was conducted. Despite the limitations of the enumeration of microbes by the petri-plate method to examine the diversity of various microbes that are present in the environment, it is a powerful method that has contributed substantially to the knowledge of microbiology.

Evaluation of the efficacy of PAM was done to enumerate bacterial diversity using M9, NM medium, PAM with Yeast extract, PAM with Peptone and PAM with Yeast extract and peptone media; based on different colony morphologies and characteristics. The bacterial diversity of a high phosphate contaminated water sample was investigated. For fast screening of the samples morphologically distinctive colonies appearing on the plates based on standard morphological characters e.g., cell shape, colour, diameter, outline, elevation, translucency etc were measured.

Among the media evaluated it was observed that maximum number of diversity was observed on PAM medium with Yeast extract and peptone. (Table 5). Efficiency of PAM for the isolation of potential phosphate accumulators was checked against Minimal medium (M9), NM medium, PAM with Yeast extract, PAM with Peptone and PAM with Yeast extract and peptone. The percentage of phosphate accumulators among heterogenous population were 68, 60, 40, 30, 16, 16 and 4 in PAM, PAM with Peptone, PAM with Yeast extract, PAM with Yeast extract and peptone, Nutrient agar media, M9 medium and NM medium respectively (Table 5).

TABLE 5

Comparative study of different media for optimization of isolation and enumeration of phosphate accumulating bacteria and diversity study.

| Sl. No. | Media used | Total heterogenous CFU | Diversity | Phosphate accumulators (% of the heterogenous) |
|---|---|---|---|---|
| 1 | Nutrient Agar | 3.11 | 20 | 16 |
| 2 | PAM Agar | 2.47 | 20 | 68 |
| 3 | PAM + Yeast extract | 2.74 | 22 | 40 |
| 4 | PAM + Peptone | 2.73 | 15 | 60 |
| 5 | PAM + Yeast extract + Peptone | 2.97 | 25 | 30 |
| 6 | NM Agar media | 2.64 | 18 | 4 |
| 7 | M9 medium | 2.21 | 3 | 16 |

The results suggest that PAM is most suitable as a synergistic microbiological growth medium composition for preferential screening of phosphate-accumulating microorganisms that grow on the culture medium, under the conditions chosen, in the presence of the other microorganism on that particular plate.

Example 3

Screening several thousands of PAOs using quantitative methods requires investment of time, labour and chemicals. Therefore, in the present investigation an attempt has been made to develop a new protocol based upon visual observation, for a quick and reliable detection of PAOs. Therefore, it was envisaged to modify the PAM medium by incorporating TBO; a blue-coloured dye that decolorizes owing to the drop in the concentration of phosphate in the medium, as an indicator to quickly evaluate the level of phosphate accumulation based upon visual observations. The metachromatic activity of poly(P) allows for staining the cells with TBO within cellular vacuoles. TBO has been used to identify the nonradioactive poly(P) species obtained from biological systems after separation by PAGE. We used a methodology that is applicable for poly(P) species resolved by PAGE that visualizes linear poly(P) species less than 5 Pi units long, as well as Pi and the trimetaphosphate ion $(P_3O_9)^{3-}$. This method involves hydrolysis of separated poly(P) species to Pi, followed by complexation of the product Pi with molybdate and the cationic dye methyl green. However, to the best of our knowledge this is the first report of directly using TBO in a microbiological growth media as an indicator dye for visual observations, to quickly evaluate the level of PAOs.

Figure 2:
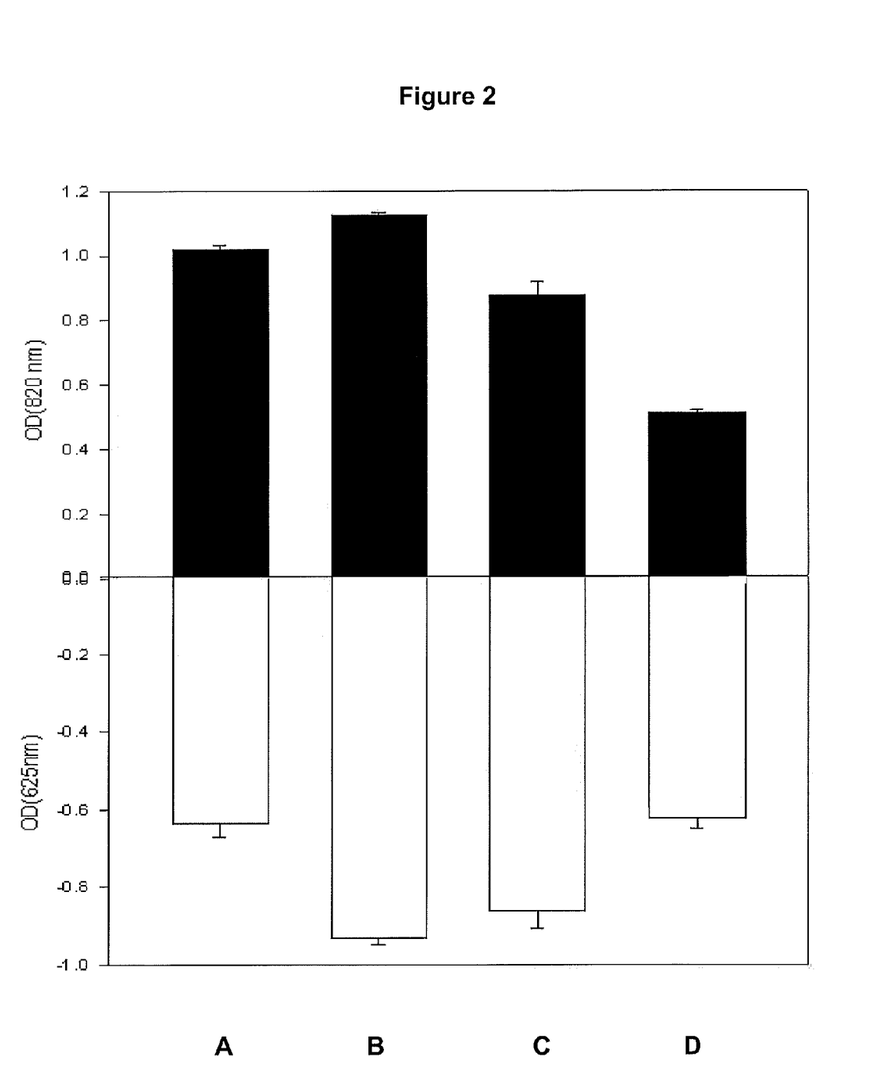
FIG. 2: Qualitative (□) and Quantitative (■) analysis of bacterial strain NBRI1213 MTCC 8708 grown in PAM medium containing 0.01 (A); 0.025 (B); 0.05 (C) and 0.1 (D) mg/ml of Toluidine Blue-O, at 28° C. for 2 days. The data depicted are mean of three independent experiments. The influence of TBO on the growth of bacterial strain NBRI1213 MTCC 8708 an efficient phosphate accumulator was compared on quantitative basis after incubation in PAM medium containing 0.01, 0.025, 0.05, and 0.1 mg/ml TBO for 2 days. The TBO dye concentration 0.025 mg/ml correlated well with quantitative assay and was used for further studies (FIG. 2). Therefore, a concentration of 0.025 mg/ml TBO was used to formulate the new medium. This PAM growth medium containing 0.025 mg/ml TBO was designated as PAM-TBO.

The influence of TBO on the growth of bacterial strain NBRI1213 MTCC 8708 an efficient phosphate accumulator was compared on quantitative basis after incubation in PAM medium containing 0.01, 0.025, 0.05, and 0.1 mg/ml TBO for 2 days. The TBO dye concentration 0.025 mg/ml correlated well with quantitative assay and was used for further studies (FIG. 2). Therefore, a concentration of 0.025 mg/ml TBO was used to formulate the new medium. This PAM growth medium containing 0.025 mg/ml TBO was designated as PAM-TBO.

Screening of PAOs deploying both qualitative and quantitative assays gave similar results, indicating that there is a correlation between a qualitative and a quantitative assay. However, in a qualitative assay with PAM-TBO, it was possible to quickly distinguish the two groups of bacteria without any need for time consuming biochemical methods usually involved in the quantitative assay of PAOs. These results suggest that PAM-TBO is most suitable as a formulation for the initial screening of PAOs.

These results indicate that PAM-TBO is most suitable as a synergistic composition for the initial screening of phosphate accumulators.

Example 4

Figure 3:
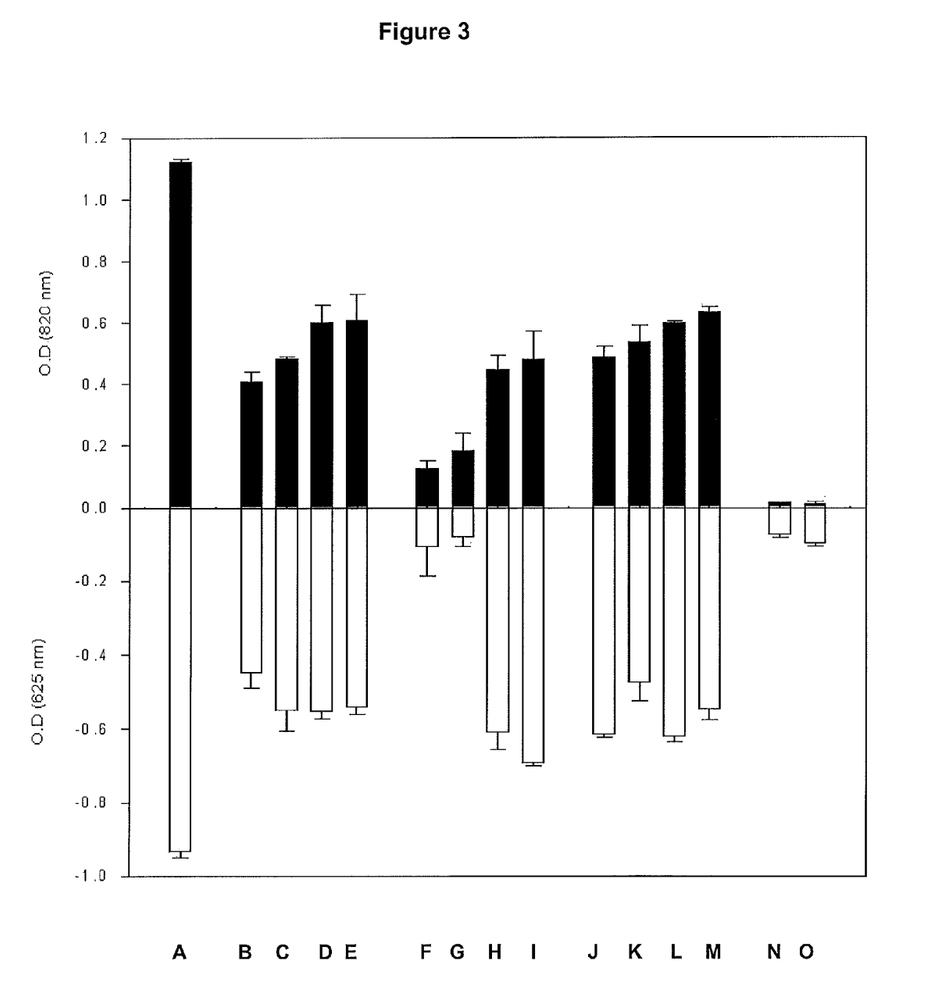
FIG. 3: Qualitative (■) and quantitative (☐) analysis of the effect of various carbon, nitrogen and salts on Phosphate accumulation ability of NBRI1213 MTCC 8708 were monitored in the presence of various carbon, nitrogen and salts.

An investigation was carried out to assess the effect of various carbon, nitrogen and salts on Phosphate accumulation ability of NBRI1213 MTCC 8708 using PAM-TBO. The results are illustrated in FIG. 3 of the drawings accompanying this specification. Qualitative (■) and quantitative (□) analysis of the effect of various carbon, nitrogen and salts on Phosphate accumulation ability of NBRI1213 MTCC 8708 were monitored in the presence of various carbon, nitrogen and salts. FIG. 3A illustrates that as compared with control PAM-TBO, NBRI1213 MTCC 8708 demonstrated diverse level of phosphate accumulation activity in the presence of various carbon glucose (3B), sorbitol (3C), glycerol (3D) and sucrose (3E). To check the effect of varying the carbon source maltose in PAM-TBO was replaced by these different carbons. Similarly, diversity in phosphate accumulation using varied nitrogen sources are depicted as $C_2H_7NO_2$ (3F), $KNO_3$ (3G), $NH_4NO_3$ (3H), $NH_4Cl$ (3I) and for salts it is shown as $Na_2CO_3$ (3J), $KCl$ (3K), $Na_2SO_4$ (3L) and $MnSO_4$ (3M). To check the effect of change in nitrogen source $(NH_4)_2SO_4$ (3A) was replaced by other nitrogen sources. The pattern of phosphate accumulation by NBRI1213 in qualitative assay with PAM-TBO correlated well with the quantitative assay. The potential of Tn5 mutants of NBRI1213 viz; NBRI1213-4052 (3N) and NBRI1213-4053 (3O) for phosphate accumulation was assessed by incubating them in PAM-TBO at 28° C. for 2 days.

This observation further augments well for the use of PAM-TBO for qualitative analysis to detect the effect of various physiological factors on phosphate accumulators, based upon visual observation. Pure culture evaluation using PAM-TBO may be a useful tool in search of phosphate accumulating strains better suited for soil environments where physiological factors may constitute a limitation for phosphate accumulation.

Example 5

Further investigation was carried out to assess the probability of an early detection of the effect of various physiological parameters and screening efficiency of phosphate-accumulation defective mutants by using PAM-TBO. An experiment was conducted to screen 500 phosphate accumulation-defective Tn5 mutants of NBRI1213 MTCC 8708. Based upon visual observations, owing to their incapability to decolorize TBO efficiently, as compared with NBRI1213 MTCC 8708 (FIG. 3A), two mutants—NBRI1213-4052 (3N) and NBRI1213-4053 (3O) were easily distinguishable by day 2. Quantitative analysis further confirmed the non phosphate accumulation ability of the mutants (FIG. 3). These findings demonstrate that there is a correlation between the pattern of phosphate accumulation by the mutants in qualitative assay and quantitative assay. The above example thus shows that using this simple protocol, it is indeed possible to screen phosphate accumulation defective mutants.

Example 6

We evaluated the efficacy of PAM to enumerate total heterogenous count, diversity and percentage of phosphate accumulators from various environments like soil, water and sludge which is indicated in Table 6.

TABLE 6

Studies on total heterogenous count, diversity and percentage of phosphate accumulators from different ecosystems

| Sl. No | Sample | Total heterogenous CFU | Diversity | Phosphate accumulators (% of the heterogenous) |
|---|---|---|---|---|
| 1 | Soil (Mud soil) | 6.20 | 8 | 36 |
| 2 | Soil (Indo-china border soil) | 5.42 | 6 | 20 |
| 3 | Water (Allahabad) | 3.70 | 3 | 40 |
| 4 | Water (Dinapur) | 5.19 | 5 | 35 |
| 5 | Sludge (Jamnagar) | 7.40 | 8 | 64 |

The above results suggest that PAM is suitable as a synergistic composition for screening of phosphate-accumulating microorganisms from various environmental sources.

Example 7

To effectively evaluate the potential application of PAM-TBO assay in screening possible PAOs in environmental samples, different kinds of PAOs were isolated from soil, water and activated sludge represented by fungi, actinomycetes and bacteria (Table 7). The results suggest that PAM-TBO medium is very effective to evaluate phosphate accumulation in all kinds of microorganisms such as bacteria, fungi and actinomycetes.

TABLE 7

Phosphate accumulation studies on different microorganisms.

| Sl. No. | Organisms studied | Phosphate accumulation [mM per gm biomass] |
|---|---|---|
| 1 | Bacteria | 132.77 |
| 2 | Actinomycetes | 0.246 |
| 3 | Fungi | 60.0 |

Example 8

The colorimetric reaction as conceived in the present invention can be applied in a novel and extremely high-throughput manner to detect individual microbial isolates, such as colonies growing on a PAM Petri plate. For example, colonies of a microbe being screened can be plated on a growth medium containing the assay solution of the present invention. The expression "high throughput" as used herein shall be understood to mean that different microbial isolates are rapidly prepared and analyzed. Data regarding the color of each sample are stored in a data library. The procedure is advantageously accomplished under program control and is automatically controlled by, for example, a microprocessor or other computer control device. The expression "program control" as used herein shall be understood to mean the equipment used herein in providing the plurality of environmental samples in automated and controlled manner by a microprocessor or other computer control devices.

Fast decolorization of the dye is an indicator of a superior phosphate accumulating microbe. Therefore, adaptation of PAM-TBO assay in screening possible PAOs in environmental samples for microtitre plate assay enhanced the effectiveness of the assay system. The assays were conducted using 96 well plates. The screening media used in the study was PAM-TBO employing a range of concentrations of $Na_2HPO_4$ and $KH_2PO_4$ (47, 94, 200, 300, and 500 mM) as phosphate sources in PAM-TBO medium.

TABLE 8

Standardization of phosphate concentration for qualitative screening of high and low phosphate accumulating bacteria using PAM-TBO microtitre plate assay method.

| | Phosphate concentration | | | | |
|---|---|---|---|---|---|
| | 47 mM | 94 mM | 200 mM | 300 mM | 500 mM |
| | Level of decolorisation | | | | |
| High PAB (NBRI-1213 MTCC 8708) | + | + | + | + | +++ |
| Low PAB (NBRI-28 MTCC 1302) | + | +++ | +++ | +++ | ++++ |

("++++" denotes control non-decolorized media; "+++", denotes minimum decolorization and "+" denotes maximum decolorization)

It is evident from Table 8 that high and low phosphate accumulators can be easily distinguished using phosphate concentration in the range of 94-300 mM by visual observations after 24 hours of growth. We opted for 94 mM for further work as it was optimally suited for screening wider range of phosphate accumulators.

Figure 4:
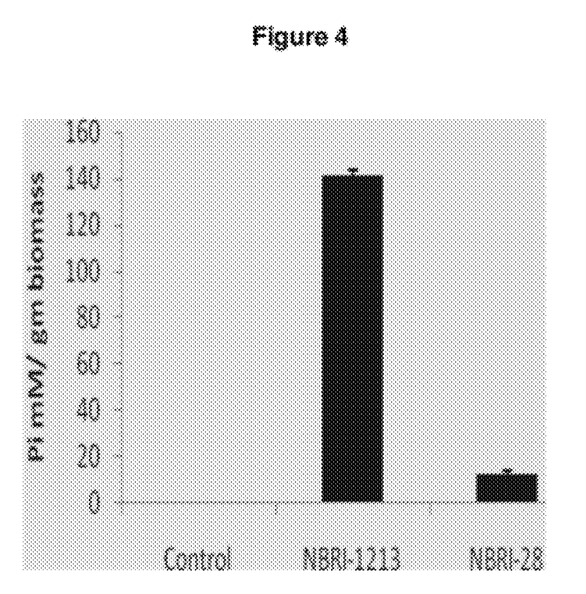
FIG. 4: Quantitative analysis of efficient/high (NBRI1213 MTCC 8708) and low phosphate (NBRI-28 MTCC 1302) accumulating bacteria grown in PAM-TBO medium, at 28° C. for 2 days. The data are means of three independent experiments.

FIG. 4 clearly demonstrates that among the 2 strains (NBRI1213 MTCC 8708 and NBRI-28 MTCC 1302) tested, based upon visual observation, the highest limit of decolorization of TBO was maximum in NBRI1213 MTCC 8708 and minimum in NBRI-28 MTCC 1302 (Table 9)

TABLE 9

| Qualitative analysis | | | |
|---|---|---|---|
| Strains | Control | NBRI-1213 | NBRI-28 |
| Level of media colour | ++++ | + | +++ |

At 94 mM phosphate concentration, the microtitre plate assay used for quantitative analysis further confirmed the phosphate accumulation ability of the strains categorized as high and low phosphate accumulators (Table 9) (FIG. 4). In Table 9, "++++" denotes control non-decolorized media; "+++", denotes minimum decolorization and "+" denotes maximum decolorisation. Strain NBRI1213 MTCC 8708 showed maximum decolorisation on qualitative as well as quantitative basis whereas in Strain NBRI-28 MTCC 1302 phosphate accumulation was low qualitatively and quantitatively. Therefore, the results allowed us to conclude that qualitative analysis of phosphate accumulation correlated well with quantitative analysis of low and high phosphate accumulating bacteria.

The above results indicate that using the synergistic composition containing PAM-TBO, it is possible to quickly screen on qualitative basis, the phosphate accumulators. Qualitative analysis of the phosphate accumulation by various groups, correlated well with grouping based upon quantitative analysis of bacteria isolated from environment. However, unlike quantitative analysis methods which involve time consuming biochemical procedures, the time for screening phosphate accumulation bacteria by the process of the present invention is significantly reduced using a simple protocol.

Certain modifications and improvements will occur to those skilled in the art upon a reading of the foregoing description. The above-mentioned examples are provided to serve the purpose of clarifying aspects of the invention and it will be apparent to one skilled in the art that they do not serve to limit the scope of the invention. All modifications and improvements have been deleted herein for the sake of conciseness and readability but are properly within the scope of the present invention. It is understood that the foregoing detailed description is given merely by way of illustration and that modification and variations may be made therein without departing from the spirit and scope of the invention.

ADVANTAGES OF THE INVENTION

In the present invention, we have arrived at a novel method useful for screening phosphate accumulating microorganisms isolated from soil, water and sludge samples.

The method is useful for screening of microbial isolates for phosphate accumulation by quantitative assay.

Color based PAM-TBO medium efficiently screen P-accumulating microorganisms qualitatively and allows many PAOs to be screened, based upon visual observations without much investment of time, labour and chemicals, as compared with quantitative assay.

Isolation of efficient phosphate accumulating bacteria thus selected using PAM and PAM-TBO media can be effectively used for phosphate bioremediation for improving the water quality of eutrophic water bodies.

What is claimed is:

1. A synergistic composition useful as a microbiological growth medium for rapid screening of phosphate accumulating microorganisms, wherein said composition comprises:
   1.0 to 10.0 g/l of sodium citrate,
   1.0 to 5.0 g/l of $(NH_4)_2SO_4$,
   0.1 to 10.0 g/l of NaCl,
   0.1 to 1.0 g/l of $CaCl_2$,
   0.1 to 1.0 g/l of $MgSO_4.7H_2O$,
   5.0 to 15.0 g/l of $Na_2HPO_4$,
   1.0 to 30.0 g/l of $KH_2PO_4$,
   0.05 to 10.0 g/l of Maltose, and
   0.01 to 0.1 g/l of Toluidine Blue-O.

2. The composition according to claim 1, wherein said composition comprises:
   4.0 g/l of sodium citrate,
   2.5 g/l of $(NH_4)_2SO_4$,
   0.5 g/l of NaCl,
   0.25 g/l of $CaCl_2$,
   0.25 g/l of $MgSO_4.7H_2O$,
   12.8 g/l of $Na_2HPO_4$,
   3.0 g/l of $KH_2PO_4$,
   1.0 g/l of Maltose, and
   0.025 g/l of Toluidine Blue-O.

3. A process for screening phosphate accumulating microorganisms, wherein said process comprises:
   (a) incubating the microorganisms in the composition according to claim 1 for a period of 1 to 15 days at a temperature of 15° C. to 46° C. under shaking to obtain a culture; and
   (b) harvesting the culture of step (a) to obtain a supernatant; and
   (c) measuring the optical density of the supernatant obtained in step (b) at 625 nm to assess decolorization of the dye as an indicator of a superior phosphate accumulating microbe.

4. The process according to claim 3, wherein the incubation is conducted at a temperature of 28° C. for 2 days.

5. The process according to claim 3, wherein the phosphate accumulation ability of the microorganisms is in the range of 1000 mM to 1 M Pi content per gm biomass of the microorganisms.

6. The process according to claim 3, wherein said microorganisms are bacteria, actinomycetes, fungi, or a combination thereof.

7. The process according to claim 3, wherein prior to said incubating the microorganisms in the composition, said microorganisms are subjected to carbon, nitrogen, salts, or a combination thereof.

8. The process according to claim 3, wherein said process is automated and controlled by a microprocessor or other computer-controlled device.

9. A kit for screening phosphate accumulating microorganisms comprising:
   the composition according to claim 1;
   at least one screening vessel; and
   instructions for use.

\* \* \* \* \*